(12) United States Patent
Mupdende et al.

(10) Patent No.: US 8,931,350 B2
(45) Date of Patent: Jan. 13, 2015

(54) ROPE TEST STAND

(75) Inventors: Ilaka Mupdende, Neu-Ulm (DE);
Norbert Stanger, Attenweiler (DE)

(73) Assignee: Liebherr-Components Biberach GmbH, Biberach An der Riss (DE)

(*) Notice: Subject to any disclaimer, the term of this patent is extended or adjusted under 35 U.S.C. 154(b) by 0 days.

(21) Appl. No.: 14/113,780

(22) PCT Filed: Apr. 26, 2012

(86) PCT No.: PCT/EP2012/001795
§ 371 (c)(1),
(2), (4) Date: Nov. 15, 2013

(87) PCT Pub. No.: WO2012/146380
PCT Pub. Date: Nov. 1, 2012

(65) Prior Publication Data
US 2014/0109682 A1    Apr. 24, 2014

(30) Foreign Application Priority Data
Apr. 26, 2011  (DE) .......................... 10 2011 018 535

(51) Int. Cl.
*G01N 3/08* (2006.01)
*G01N 3/32* (2006.01)
(Continued)

(52) U.S. Cl.
CPC .. *G01N 3/32* (2013.01); *G01N 3/08* (2013.01); *B66C 15/00* (2013.01); *B66D 1/54* (2013.01); *G01N 2203/028* (2013.01)
USPC ................... 73/829; 73/828; 73/826; 73/812; 73/808

(58) Field of Classification Search
USPC ............................ 73/812–820, 826, 828–830
See application file for complete search history.

(56) References Cited

U.S. PATENT DOCUMENTS

| 2,632,325 | A | * | 3/1953 | Norcross ........................ 73/829 |
| 7,267,241 | B2 | * | 9/2007 | Franzen et al. ............... 212/278 |
| 7,634,949 | B2 | * | 12/2009 | Lodge et al. .................... 73/828 |

(Continued)

FOREIGN PATENT DOCUMENTS

| DE | 29503416 U1 | 7/1995 |
| EP | 1103511 A2 | 5/2001 |

(Continued)

OTHER PUBLICATIONS

International Search Report mailed Mar. 5, 2012 for priority application PCT/EP2012/001795.

*Primary Examiner* — Lisa Caputo
*Assistant Examiner* — Jonathan Dunlap
(74) *Attorney, Agent, or Firm* — Troutman Sanders, LLP; Ryan A. Schneider

(57) ABSTRACT

A cable test bench for testing a test cable to establish service life, replacement age, number of flex cycles, and/or winding behavior, has a deflection system including at least one deflector roll to deflect the test cable, one test cable drive to wind and unwind the test cable via the deflection system, and one test load to load the test cable. The cable test stand has an additional cable test drive for winding and unwinding a safety cable and/or the named test cable, and a control device for controlling the additional cable drive and/or the test cable drive in a manner wherein the two are adjusted to each other, in such a manner that the load of the test cable can be adjusted differently for different test cable segments and/or different winding directions and/or different winding cycles and/or different phases of a winding cycle.

19 Claims, 5 Drawing Sheets

(51) Int. Cl.
  *B66C 15/00* (2006.01)
  *B66D 1/54* (2006.01)

(56) References Cited

U.S. PATENT DOCUMENTS 8,544,339 B2 * 10/2013 McKee et al. .................. 73/829
2004/0104191 A1 * 6/2004 Franzen et al. ............... 212/283

FOREIGN PATENT DOCUMENTS

| JP | H07172763 A | 7/1995 |
| JP | H10318741 A | 12/1998 |
| JP | 2000327272 A | 11/2000 |

* cited by examiner

ROPE TEST STAND

CROSS-REFERENCE TO RELATED APPLICATIONS

This application is a US National Stage of International Application No. PCT/EP2012/001795, filed 26 Apr. 2012, which claims the benefit of DE 10 2011 018 535.6, filed 26 Apr. 2011, both herein fully incorporated by reference.

BACKGROUND OF THE INVENTION

1. Field of the Invention

The present invention relates to a cable test bench for testing a test cable to establish service life, replacement age, number of flex cycles, and/or winding behavior, having a deflection system comprising at least one deflector roll to deflect the test cable, one test cable drive to wind and unwind the test cable via the deflection system, and one test load to load the test cable.

2. Description of Related Art

Cables in safety applications, such as steel and fiber ropes of hoisting machines such as cranes, must be tested under test bench conditions to establish their service life, their replacement age, and their allowed number of flex cycles, in order to be able to make reliable determinations of how long the affected cable may be used in operation. For this purpose, cable test stands are typically used wherein a cable being tested is guided around at least one deflector roll under a defined load, in order to simulate a corresponding flexing process under load. Multiple cable rolls are typically used for this procedure in order to simulate opposing flexing processes, wherein the test load is hoisted and lowered in multiple test cycles, such that the test cable is subjected to corresponding flex cycles in a repeating winding and unwinding. Conventional cable test benches in this case regularly determine the number of cable flex cycles before replacement age and up to the breaking of the cable resulting from alternating movement of the cable over the at least one cable roll, with modified tensile force on the cable—for example by suspending various different test loads—or with smaller or larger ratios of the diameter of the cable roll to the diameter of the cable. In this way, it is possible to test cables made of different materials and having different braid pattern, and to determine the replacement age and the service life together with the number of flex cycles.

To date, in order to obtain not only results on the simple number of flex cycles, but also to arrive at results on the service life of a cable used in a wire rope drive system having a cable drum and cable rolls—as in the case of crane hoists or crane boom control systems, for example—cable test stands have been used which consist of a tower with trusses, or two towers with a connector, wherein a cable winch is usually arranged at the foot of the tower, from which the test cable is guided to the top of the tower, the trusses, or the center of the connector via multiple deflector rolls to a load hook reeved with one or multiple passes. A test load is attached to the load hook, and the hoisting and lower thereof creates a test cycle with a constant load. In order to prevent the load from falling if the cable breaks, the load can be guided on perpendicular rails which have a fall arrestor similar to that of passenger elevators. However, after a break of the cable, it is not easy to reset the test stand for further use, and sometimes requires a great deal of time.

A further disadvantage of cable test stands to date is that they only emulate the load cycles which occur in cranes and hoisting machines to a limited degree. The cable test stands typically only have the chance to carry out a test cycle with hoisting and lowering using the particular test load suspended from the stand. As a result, the cable has substantially the same tensile load both during hoisting and lowering, which in this case only varies as a result of differences in the degree of efficiency. However, this does not correspond to the actual application of a cable in a cable drive system, for example in a lifting unit of hoisting machines. By way of example, cranes typically hoist a load, set down the load once hoisted, and move on to the next load with still raised with no load, and/or are lowered with no load. In this case, a complete load cycle on the lifting gear is typically approximately 50% hoisting under load, and 50% lowering without load. According to the application, however, lifting gear load cycles can occur with the opposite load profile, wherein the load is received at the maximum hoisting height, or the load is released in the lowered position—as in the case of tunnel construction sites, for example. In this case, the lifting gear load cycle typically comprises 50% lowering under load, and 50% hoisting without load.

These load cycles occurring in practice in cranes or other hoisting machines can only be insufficiently emulated by cable test stands used to date, because it is generally not possible to set down the load or pick up the load after the hoisting path has been traveled. However, this would be important for determining the cable service life in a manner appropriate to actual practice.

In addition, cable test stands to date only insufficiently determine the winding behavior of the cable as appropriate to actual practice. According to experience, if the test load is hoisted and lower under constant cable tension, and accordingly the test cable is wound and unwound under a constant load, the test cable demonstrates good winding behavior. However, in practice, the winding behavior of the cable is altered when the cable is wound without a load as a result of the load being set down at a height, and/or when the cable is unwound without a last as a result of the load being set down after being lowered. In addition, such load cycles in the winding and unwinding of the cable also influence the life cycle of the cable, which cannot be sufficiently emulated by cable test benches to date. The winding behavior under alternating cable tension is also specifically of interest when windings occur in multiple layers—meaning that the cable is not wound only in one layer, but is wound around the winch roll in multiple layers—because in this case the cable is subjected to loads in a different manner as a result of cable layers lying one on top of the other. It has also not been possible to reproduce this in test stands to date.

The problem addressed by the present invention is therefore that of creating an improved cable test stand of the type named above which avoids the disadvantages of the prior art and develops the same in an advantageous manner. In particular, the loads which actually occur in cables of hoisting machines such as cranes should be emulated in a manner which is appropriate to actual practice, without the need for this to be achieved at the cost of complex handing to carry out the test cycles, such as suspending and un-hanging additional test loads, and the cable test stand should have a simple construction.

BRIEF SUMMARY OF THE INVENTION

According to the invention, the problem as named above is addressed by a cable test stand for testing a test cable to establish service life, replacement age, allowed number of flex cycles, and/or winding behavior, having a deflection system comprising at least one deflector roll to deflect the test cable, a test cable drive to wind and unwind the test cable via the deflection system, and one test load to load the test cable, characterized by an additional cable drive for the purpose of winding and unwinding a safety cable and/or the test cable, as well as a control device for the purpose of controlling the additional cable drive and/or the test cable drive in a manner wherein the two are adjusted to each other, in such a manner that the load of the test cable can be adjusted differently for different test cable segments and/or different winding directions and/or different winding cycles and/or different phases of a winding cycle.

It is also suggested that two cable drives be configured on the cable test stand, by means of which it is possible to alter the load on the test cable for different phases of the test cycles, without the need to exchange or modify the test load suspended on the test cable in this case. In addition to the test cable drive used to date, an additional cable drive is included, wherein the test cable force is altered by said additional cable drive being switched on or off. According to the invention, the cable test stand has an additional cable test drive for the purpose of winding and unwinding a safety cable and/or the named test cable, as well as a control device for the purpose of controlling the additional cable drive and/or the test cable drive in a manner wherein the two are adjusted to each other, in such a manner that the load of the test cable can be adjusted differently for different test cable segments and/or different winding directions and/or different winding cycles and/or different phases of a winding cycle. In this way, it is possible to vary the load applied to the test cable without altering the test load, by means of a stronger or weaker application of the additional drive and/or increasing or reducing the cable force applied by the additional cable drive, without reconfigurations of the cable test stand—such as replacement of the test load—being necessary for this. With the variably controlled additional cable drive, the load acting on the test cable can be easily varied over the length of the test cable as the same is wound and unwound.

In one implementation of the invention, the control device can be designed in such a manner that the load of the test cable can be varied by stronger and/or weaker application of the additional cable drive during a winding process, and particularly during a hoisting process and/or during a lowering process. As a result, it is possible to simulate the changing loads which occur in practice during a hoisting or lowering process—for example in a cable-operated boom of a derrick crane—for example when a derrick crane boom is drawn up and the load on the cable drive lessens as a result of the lever arm becoming smaller.

As an alternative or in addition thereto, the control device can also function to vary the load on the test cable by applying the additional drive to different test cable segments, and/or to different points in the path traveled by the test load, at a greater or lesser strength. As a result, it is possible to simulate varying lift heights and/or the lowering or picking-up of a load at different lift heights, such that the cable is subjected to different loads at different cable segments, which effects the service life and/or replacement age of the cable at corresponding load cycle counts.

As an alternative or in addition thereto, the control device can also be designed in such a manner that it is possible to carry out test cycles with full loads during hoisting and no loads during lowering, and to carry out test cycles with no load during hoisting and with full loads during lowering. As a result, it is possible to emulate lifting gear cycles particularly in cranes or hoisting machines with approximately 50% lifting under load and 50% lowering without load, or vice-versa—depending on the application—with 50% hoisting under load and 50% lowering under load, in order to determine the replacement age and the service life of a hoisting machine cable.

In one implementation of the invention, the named additional cable drive can be used for the purpose of winding and unwinding a safety cable which is preferably routed via its own cable reeving to the test load. Said safety cable in this case advantageously serves the purpose not only of securing the test load in the event of the test cable breaking—which is advantageous in and of itself, because as a result it is possible to dispense with the guide rails and arresting device which can been used in conventional devices to date—but it can also be used to vary the cable load which acts on the test cable by applying the safety cable at a greater or lesser strength as result of the additional cable drive being switched on. In one implementation of the invention, the test cable can particularly be wound and unwound by the test cable drive, and the safety cable can be wound and unwound by the additional cable drive, in such a manner that it is possible to effect a hoisting or lowering of the test load, as desired, by the test cable alone, or by the safety cable, or by both the test cable and the safety cable. If the test load shall be hoisted by the test cable alone, the safety cable merely follows with substantially no load. If the opposite will occur, with hoisting with no load on the test cable, the test load is hoisted by the safety cable, and the test cable merely follows. In addition to these single hoisting or lowering processes, mixed hoists can be carried out, wherein the test load is distributed across the test cable and the safety cable, and therefore is hoisted or lowered by both the test cable and the safety cable. The distribution of the test load in this case can occur in such a manner that part of the path traveled in a hoisting or lowering process is partially or entirely taken over by the safety cable, or in such a manner that the safety cable takes over part of the test load over the entire path of travel, in order to execute a hoisting or lowering process with a reduced load on the hoisting cable, wherein optionally the part of the load which is taken over by the safety cable can also be varied during a hoisting or lowering process in order to emulate changing loads, in the manner named above, such as may occur when a crane boom is drawn up or lowered down, by way of example.

As an alternative or in addition thereto, in one implementation of the invention, the test cable can be routed via a cable reeving to the test load, and routed via the deflection system to both the test cable drive and the named additional cable drive or to a further additional cable drive, wherein the named control device is advantageously designed in such a manner that the test cable drive and the additional cable drive can be operated in opposite directions, in such a manner that the test cable can be spooled from the test cable drive to the additional cable drive, and/or in the opposite direction from the additional cable drive to the test cable drive. If only one additional cable drive is included, instead of the safety cable named above, the test cable can be routed to the additional cable drive in a corresponding test procedure. However, a further additional cable drive can be advantageous included, wherein the test cable is routed to the same in the manner named above, while the safety cable is spooled to the other additional cable drive in the manner named above, said safety cable being preferably routed via a separate cable reeving to the test load. In this way, on the first hand, the test load can be secured in the event of the test cable breaking. On the other hand, it is possible to carry out different test modes for the test cable without modifications, particularly test modes wherein different load conditions are applied to the test cable and/or simulated, in the manner named above, by varying the application of the safety cable. In addition, test modes wherein the test cable is spooled from the test cable drive to the additional cable drive, and vice-versa, can be carried out without the named safety cable being applied.

In this manner, a longer section of the test cable can be subjected to flex cycles regardless of the height of the cable test stand and the hoist path available to the test load. In particularly, it is also possible to test very long cables in this way. By way of example, the test load can be lifted off the ground a slight distance by the test cable drive and/or the additional cable drive. Then, in this position, the test cable can be spooled from one to the other roll or vice-versa under full load or partial load. The spooling of the maximum cable length is only dependent on the cable storage capacity of the drum, and not on the height of the cable test stand. As a result, it is possible to test the spooling behavior on the drum with multiple wound layers, by way of example. Because the load is near the ground, it is also possible to do this without the load being secured against falling.

In addition, however, in this cable test mode, different load states can be provided for the test cable by means of lowering the test load partially or entirely to the ground. In order to increase the number of load states which can be achieved, in one advantageous implementation of the invention, the test load is subdivided into multiple partial test loads, such that it is possible to vary the resting residual test load applied to the test cable by setting down a different number of partial loads.

By at least partially setting down the test load, it is also possible to carry out entirely unloaded, or partially-loaded hoisting or lowering cycles without application of the safety cable named above, wherein by changing the point in time at which the test load is set down, it is also possible to execute only parts of a hoisting or lowering cycle, or to execute hoisting or lowering cycles of differing lengths and with reduced load or no load.

In order to be able to exactly tune the operation of the additional cable drive to the operation of the test cable drive, or the other way around, in one advantageous implementation of the invention, the test cable drive and/or the additional cable drive can have an electric motor as the drive device, said motor being precisely controlled by means of a variable frequency drive. In particular, said control device can have an electronic controller for the purpose of controlling the test cable drive and additional cable drive, which enables measurement of the path and force of the test cable using corresponding sensors. In one advantageous implementation of the invention, the control device has suitable detection means which are suitable for determining the drum rotations of the hoisting winch of the test cable drive and additional cable drive, to measure the rotation speed, to determine the length of cable fed out or wound in, to determine the number of load cycles, to monitor the cable state, the determine the number of lift cycles, and to determine the hours of operation and/or additional parameters which are relevant to the service life, the replacement age, the allowable number of flex cycles, and/or the winding behavior of the test cable.

The determination means for determining the replacement age and/or the service life in this case can have different designs.

The detection device of the device for establishing the replacement age advantageously has multiple, differently designed detection means for the purpose of magnetically, mechanically, optically, and/or electronically detecting multiple different cable parameters which can be evaluated individually and/or in combination with each other by the evaluation device for the purpose of establishing the replacement age. The incorporation of different cable parameters for the determination of the replacement age is based on the consideration that, depending on the load and action on the test cable, it can be a different parameter from one case to the next which indicates the wear on the cable and/or indicates the replacement age and/or demonstrates the replacement age optionally not by means of a specifically larger change of only one single parameter, but rather by smaller changes in multiple parameters.

In one advantageous implementation of the invention, said evaluation device is designed in such a manner that a removal signal is produced when at least one of the detected cable parameters and/or the change thereof exceeds an associated threshold, and also when one of all of the cable parameters which is detected or which is indirectly derived from a subgroup of the detected cable parameters, and/or the change thereof, exceeds an associated threshold.

In this case, in one advantageous implementation of the invention, different cable parameters are incorporated. According to a further aspect of the present invention, a change in an indicator profile embedded into the test cable, said indicator profile consisting of a different material than the rope fibers, is advantageous monitored. By means of such an indicator profile which is embedded into the core of the braid, or which can also be arranged between the fiber strands of the test cable, it is possible to circumvent the [problem of the] difficulty of detecting change in the fibers and/or fiber strands of the test cable itself, particularly if the design and/or the material of the indicator profile is selected such that the indicator profile shows changes more quickly than the fiber stands of the test cable, and/or it is possible to detect such changes more easily. The monitoring of such an indicator profile in the test cable in this case can also pose particular advantages in and of itself without further parameters being monitored.

In particular, the indicator profile can consist of a material which influences a magnetic field and/or is magnetically conductive and/or can be magnetized, preferably a metallic continuous profile. The detection means in this case are advantageously designed to work magnetically, wherein a magnetic field sensor can particularly be included, by means of it is possible to determine the magnetic properties of said indicator profile. In particular, the magnetic properties of the indicator profile change up a break of the indicator profile, such that a corresponding change in the magnetic flux and/or the magnetic field can be easily detected and used as an indicator of wear. If a break occurs in the magnetically conductive indicator profile, this can be detected by a magnetically inductive monitor and/or by a corresponding break in the magnetic field.

As an alternative or in addition to such a design of the indicator profile and the corresponding detection means which work magnetically, changes in said indicator profile could also optionally be monitored in a different manner based on other monitoring approaches. By way of example, the indicator profile could be designed to conduct electrically, and the electrical conductivity of the test cable and/or the indicator profile configured therein could be monitored by means of accordingly designed detection means. As an alternative or in addition thereto, a thermal conductivity of said indicator profile could be monitored, wherein in this case, the indicator profile is advantageously constructed of a material with good thermal conductance properties—for example a silver wire.

Said indicator profile, embedded in the test cable and consisting of another material than the rope fibers, is advantageously designed to be weaker—as regards its resistance to cable tension, expansion, tensile strength, bending, twisting, UV radiation, water absorption, and/or temperature—than the test cable, in such a manner that the indicator profile fails significantly faster than the test cable and/or the fiber strands thereof. In this way, it is ensured that a change in the indicator profile can be detected before the test cable fails. A break in said indicator profile still has no noticeable effect on the strength of the test cable, but can be easily determined and can be detected in a timely manner prior to the fail of the cable.

In one implementation of the invention, the detection device executes a monitoring function to determine in which cable segment a change occurs in the cable, said change being used to determine the replacement age, in order to identify the worn and/or damaged cable segment and optionally still be able to use the remaining cable—for example by separating the damaged part. In one implementation of the invention, cable path and/or cable position detection means can be functionally assigned to the detection means named above, said detection means determining the cable path traveled and/or the position of the cable segment being monitored for changes. Said cable path—and/or cable position detection means can particularly detect a cable winding position which is assumed when the cable segment which is being monitored for changes is positioned in the region of the corresponding detection device and is actually being monitored for changes. Then, from said cable winding position, a back calculation can be made in the evaluation device of which cable segment is damaged and/or worn.

According to a further advantageous aspect of the present invention, as an alternative or in addition to said magnetically inductive monitoring of an embedded indicator profile, a length of the test cable can also be monitored and used for the determination of the replacement age. The monitoring of the elongation of the test cable proceeds from the consideration that increasing wear and/or damage to the test cable and/or the same approaching the replacement age is associated with an elongation of the test cable with respect to the original state thereof, such that the monitoring of the elongation of the test cable can be used as an indicator for the replacement age. The detection device can have determination means for this purpose, to determine the elongation of the test cable, wherein the evaluation device compares the elongation as determined to an allowable maximum elongation. As soon as the elongation exceeds a pre-specified measure, the replacement age can be indicated.

A different can be used in this case to determine the elongation. In particular, in a first operating mode, the elongation of the cable—particularly the cable as a whole under load, and/or a segment of the cable—can be determined and monitored. As an alternative or in addition thereto, in a second operating mode, the elongation of the test cable can be monitored sectionally to determine whether and to what extent predetermined segments of the test cable are elongated.

According to one advantageous embodiment of the invention, the determination means for determining the elongation can have a position sensor for the purpose of detecting the position of a predetermined cable segment, as well as a cable winding position sensor for the purpose of determining the winding position at the time when the predetermined cable position is reached. Said position sensor can detect, by way of example, if an upper switch-off point for the load hook has been reached and/or if a signaling device attached to the cable, for example in the form of a marking, has reached a predetermined position along the cable path. The cable winding position sensor detects the cable winding position at this moment and/or when the named position is achieved, such that the evaluation device can determine the cable elongation based on a change in the winding position at this point. If the winding position when the predetermined position of the predetermined cable point deviates too much from a target position, the replacement age can be assumed and/or a removal signal can be output.

As an alternative or in addition thereto, multiple signaling devices, for example in the form of markings, transponders, signal reflectors, or the like can be configured distributed along the length of the test cable, thereby subdividing the test cable into multiple longitudinal sections. The determination means for determining the cable elongation determine the distance between each pair of signaling devices, wherein the evaluation device can determine the elongation of the corresponding cable segments from said distance and thereby monitor for changes. If elongations occur in one or more cable segments, which individually or in total go beyond a respective threshold for the allowable elongation, the evaluation device can output a removal signal.

In one implementation of the invention, said detection device can be designed in such a manner that a measuring device, for example an electronic measuring device, detects the appearance and/or the passing of said signaling device at a certain point along the cable path, and measures the longitudinal distance until the next signaling device, preferably at a constant cable speed. In this manner, the cable length can be divided and/or subdivided into any number of measurement points and into any number of cable segments, such that it is possible to determine the profile of extension along the entire length of the cable, and for an evaluation to be made in the evaluation device of which cable segment the threshold has been achieved in, and in which the cable must be replaced, or, if possible, to determine the replacement area—meaning the overextended cable area that must be removed.

The testing for elongation advantageously takes place under pre-specified boundary conditions, particularly pre-specified cable load, for example by suspending a test load, in order to eliminate variance of the test results due to varying boundary conditions.

As an alternative or in addition to said monitoring of the elongation of the test cable and/or of said change in the embedded indicator profile, according to a further advantageous aspect of the present invention, a change in the cross-section of the cable can be monitored and used as an indicator of the replacement age. The detection device for detecting cable changes can particularly have cross-section determination means for the purpose of determining the cross-section of the cable, particularly the surface area of the cross-section of the cable, wherein the evaluation device monitors the determined cable cross-section, particularly the determined cable cross-section surface area, for changes.

The cable cross-section can be detected in principle in many different ways. Said cable cross-section determination means can advantageously have diameter detection means to detect the cable diameter in at least two different planes, and to determine the cable cross-section surface area from said two determined cable diameters. In principle, configuration can also be contemplated wherein the cable cross-section surface area is determined and/or derived from only one cable diameter which has been determined in one plane. However, the cable cross-section and/or the cable cross-section surface area is advantageously determined from two cable diameters which have been determined in different planes which are approximately perpendicular to each other, because in this way it is possible to taken into account cross-sectional changes and/or deformations which have no impact on the strength of the test cable, and rash assumptions of wear can be prevented. High-strength test cable under transverse loads, such as those which can occur in cable rolls or on the cable winch, display ovalizing cross-sectional changes, meaning that the circular cross-section present at the outset changes to a profile pressed more flat, which does not itself damage the service life and/or strength of the test cable. However, if the cross-section changes in such a manner that the cross-section surface area is reduced, this is advantageously seen as a sign of wear occurring. The evaluation device can particularly provide a removal signal when the cable cross-section shows a predetermined narrowing, and/or reduction of the cable cross-section surface area exceeds a predetermined measure.

The determination of the diameter in this case can be carried out in different ways. By way of example, an optical scan by means of irradiation with light and a sensor configured to detect the width of the shadow could be used. In one advantageous implementation of the invention, however, a mechanical scan of the cable takes place from opposite side in order to determine the cable diameter. Preferably, at least one clamping means pair, preferably in the form of cable rolls which can be pressed against the cable, can be included, wherein a distance meter is functionally assigned to said cable rolls to measure the distance of the clamping means to each other when clamped on the cable.

In order to no negatively influence the determination of the diameter by deflecting the cable, it is possible to suspend the scanning means named above in a manner allowing movement, such that they can follow along with cable movements—particularly lateral cable movements—when they are clamped onto the cable. The pre-tensioned clamping means named above, in the form of the cable rolls, can particularly be moved relative to each other, on the first hand, and other the other hand can be moved together, perpendicular and/or parallel to the longitudinal direction of the cable, in order to make it possible to exactly determine the cable diameter even when undesired deflections of the cable occur.

The cable measurement advantageously takes place in at least two planes in order to be able to eliminate deviations of the cable cross-section from the circular shape in the determination of the cross-section surface area. For this, two cable roll pairs can be included, by way of example, which are arranged in planes which are perpendicular to each other, and which can each be elastically tensioned against each other.

In one advantageous implementation of the invention, for the determination of the replacement age of the test cable, the load spectrum acting on the cable can also be utilized—particularly the tensile loads acting on the cable and the flex cycles applies to the cable. For this purpose, a load spectrum counter can be included which detects at least the tensile load on the cable, and the number of flex cycles, as the load spectrum acting on the test cable. The determination and evaluation of this measured data is possible by means of corresponding determination means and/or detection means or sensors, wherein the measured data thereof is processed and evaluated in the evaluation device. In particular, a load sensor can detect the continuous load of the cable over the operating time of the cable. To determine the flex cycles, a rotational distance sensor on the drum of the cable winch can determine the cable length which is loaded. In the evaluation device, the load data and the cable path and/or flex cycle data can be linked together in order to determine a load spectrum which can be compared to a predetermined, allowable maximum load spectrum. If the number of the maximum, allowable load spectrum is reached, the evaluation device can output a corresponding removal signal.

For the computational determination of the load spectrum acting on the cable, in principle various different analytical approaches can be used. The approach can be explored proceeding from considerations of determining different degrees of damage based on the computational accumulation of damages for different load spectra, and to store these in the control system. In this way, given a certain pre-specification of load cycles, conclusions can be made by computation about the damage which the cable incurs accordingly, wherein a threshold can be determined which allows an estimate of the replacement age.

By way of example, a counting process can be used in the evaluation of the load spectrum present, wherein the amplitude of the loads present can be represented via the cumulative frequency thereof, for example. Because the test cable is normally not subjected only to a repeating, identical load with a constant amplitude, but rather to a load which can vary in its intensity, the load spectrum occurring in practice can be divided and/or stepped into individual rectangular spectra each with constant load and a partial load cycle count. By way of example, according to the method already known for linear damage accumulation, at this point a partial damage can be calculated for each partial spectrum by dividing the partial load cycle count by the maximum tolerable load cycle count. The partial damages of all partial spectra found in this way can be summed and used as an indication of the overall damage to the test cable. In a manner which is likewise known in and of itself, this approach for linear damage accumulation can also be modified are various ways, for example to the effect that partial spectra having load amplitudes below the fatigue limit threshold are not taken into account or are only taken into account in a limited manner.

In one implementation of the invention, the monitoring of the changes of the test cable named above, particularly the magnetic change of an indicator profile, the change of the cable elongation, and/or the change of the cable diameter, can be carried out for the purpose of determining corresponding parameters. In particular, the corresponding reference values for the corresponding parameters, particularly the magnetic conductance and/or property of the indicator profile, the original length of the cable, or the cable cross-section surface area, can be determined and/or detected on the cable test stand. In the continuing operation of the crane and/or hoisting machine, the parameters named above are then continuously and/or cyclically monitored, and are compared to the reference values determined on the cable test stand. If one or more of the parameters named above shows a deviation with respect to the corresponding reference value which exceeds an allowable degree of deviation, the crane controller can produce a removal signal.

These and other objects, features and advantages of the present invention will become more apparent upon reading the following specification in conjunction with the accompanying drawing figures.

BRIEF DESCRIPTION OF THE DRAWINGS

Various features and advantages of the present invention may be more readily understood with reference to the following detailed description taken in conjunction with the accompanying drawings, wherein like reference numerals designate like structural elements, and in which.

DETAILED DESCRIPTION OF THE INVENTION

Figure 1:
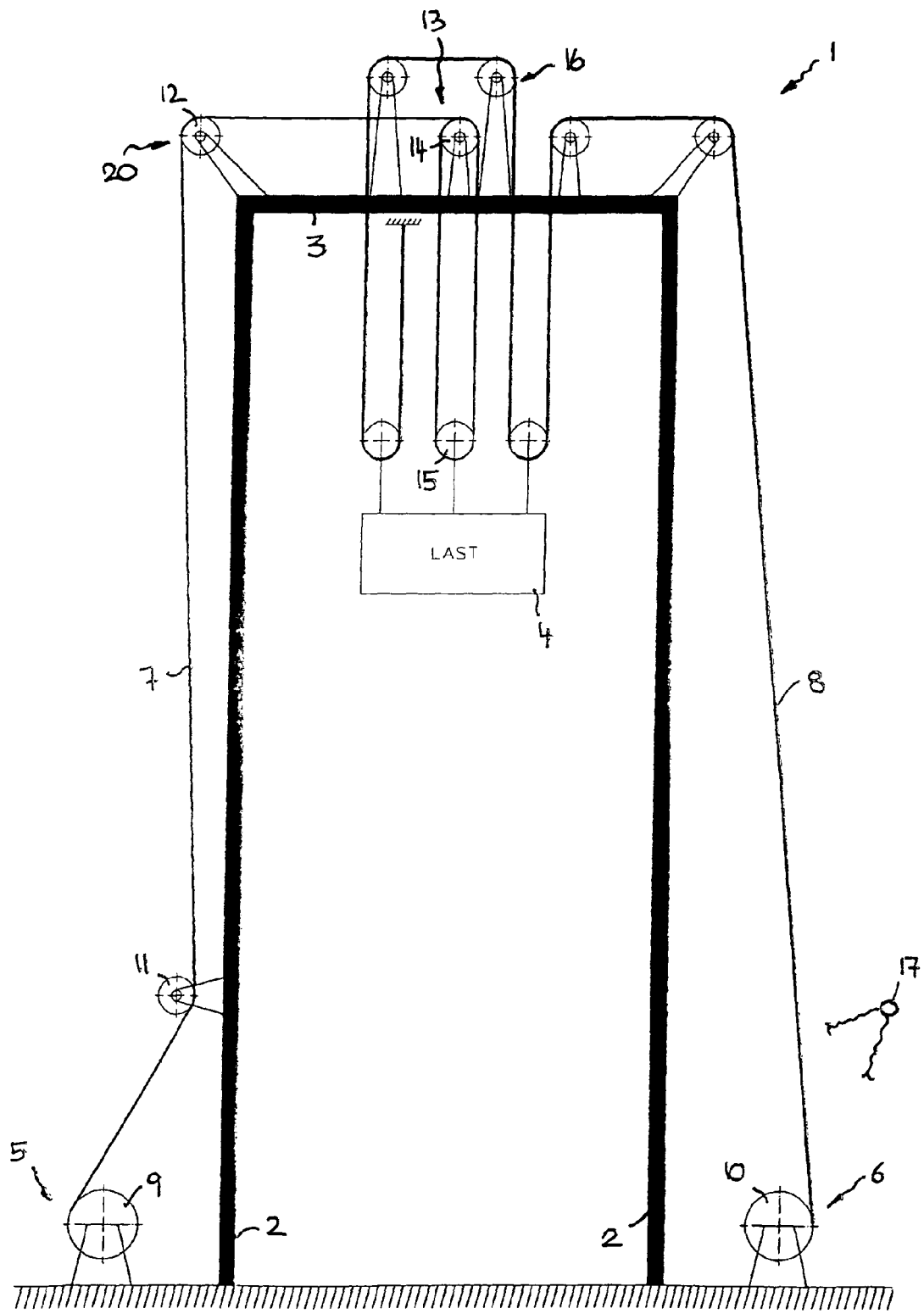
FIG. 1 shows a schematic illustration of a cable test stand according to an advantageous embodiment of the invention, wherein a test cable is guided from a test cable drive, and a safety cable is guided from an additional cable drive, via separate cable reevings, to a test load, such that it is possible to selectively hoist and lower the test load by the test cable alone, or the safety cable alone, or by the test cable and the safety cable, in order to generate changing loads on the test cable.

To facilitate an understanding of the principles and features of the various embodiments of the invention, various illustrative embodiments are explained below. Although exemplary embodiments of the invention are explained in detail, it is to be understood that other embodiments are contemplated. Accordingly, it is not intended that the invention is limited in its scope to the details of construction and arrangement of components set forth in the following description or illustrated in the drawings. The invention is capable of other embodiments and of being practiced or carried out in various ways. Also, in describing the exemplary embodiments, specific terminology will be resorted to for the sake of clarity.

It must also be noted that, as used in the specification and the appended claims, the singular forms "a," "an" and "the" include plural references unless the context clearly dictates otherwise. For example, reference to a component is intended also to include composition of a plurality of components. References to a composition containing "a" constituent is intended to include other constituents in addition to the one named.

Also, in describing the exemplary embodiments, terminology will be resorted to for the sake of clarity. It is intended that each term contemplates its broadest meaning as understood by those skilled in the art and includes all technical equivalents which operate in a similar manner to accomplish a similar purpose.

Ranges may be expressed herein as from "about" or "approximately" or "substantially" one particular value and/or to "about" or "approximately" or "substantially" another particular value. When such a range is expressed, other exemplary embodiments include from the one particular value and/or to the other particular value.

Similarly, as used herein, "substantially free" of something, or "substantially pure", and like characterizations, can include both being "at least substantially free" of something, or "at least substantially pure", and being "completely free" of something, or "completely pure".

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

It is also to be understood that the mention of one or more method steps does not preclude the presence of additional method steps or intervening method steps between those steps expressly identified. Similarly, it is also to be understood that the mention of one or more components in a composition does not preclude the presence of additional components than those expressly identified.

The materials described as making up the various elements of the invention are intended to be illustrative and not restrictive. Many suitable materials that would perform the same or a similar function as the materials described herein are intended to be embraced within the scope of the invention. Such other materials not described herein can include, but are not limited to, for example, materials that are developed after the time of the development of the invention.

Figure 2:
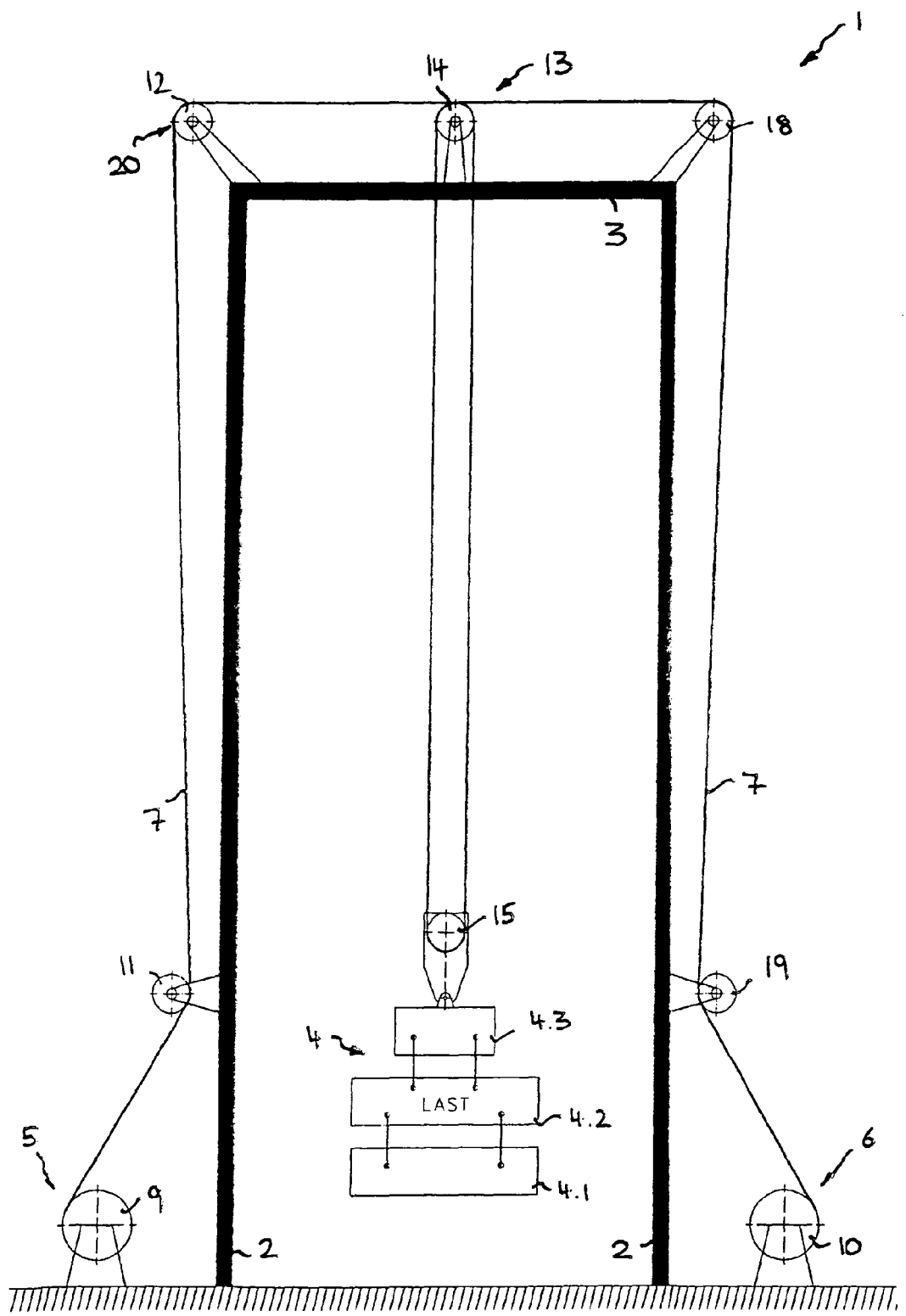
FIG. 2 shows a schematic illustration of the cable test stand in FIG. 1 in other setup condition in which the test cable is routed to the test load both to the test cable drive and to the additional cable drive, and between the two cable drives, via a reeving, such that the test cable can be spooled back and forth from one of the cable drives to the other cable drive, and vice-versa.

As FIGS. 1 and 2 show, the cable test stand 1 can be designed as a portal, and can have two vertical towers 2 which are advantageously man-size, are strongly anchored in a foundation, and are connected in the upper region thereof by a support construction 3. A test load 4 is positioned in the middle between the towers 2, and can be raised and lowered between the towers 2 below said support construction 3.

One cable drive is positioned on each tower 2, advantageously on the ground and/or in the region of the foundation of the towers 2, said cable drives being advantageously positioned opposite each other on the outside of the towers in order to not impose on the work area. In FIG. 1, the test cable drive 5 is included on the left side, and the additional cable drive 6 is included on the right side.

Instead of the design shown in FIG. 1, however, it is possible for only one tower to be included instead of two towers 2, said single tower being configured on the upper end thereof with a boom, wherein the test load is then reeved into the boom. The winches in this case can be arranged opposite about the boom on the ground, in order to accordingly route the cable via the boom to the test load and to the winches.

As FIG. 1 shows, in a first test mode, a test cable 7 can be routed from the winch 9 of the test cable drive 5 via deflector rolls 11 and 12 and a cable reeving 13, which can have one or multiple passes, to the test load. The cable reeving 13 named above can include a single-pass or multiple-pass roller packet 14 and 15 which is configured on the portal support named above on one side, and on the test load on the other side.

A safety cable 8 is likewise routed to said test load 4 from the winch 10 of the additional cable drive 6 via a separate cable reeving 16. Said safety cable 8 serves firstly as a securement against the load falling if the test cable 7 tears, but also likewise to receive and move the load according to the type of experiment and the mode of the experiment on the test cable 7. The strength of the safety cable 8 is chosen advantageously to be significantly higher than the strength of the test cable 7 with respect to the breaking load, such that it is certain that the test cable 7 will tear first, and the test load 4 will be caught by the safety cable 8 in the event that the test cable 7 tears.

The winches 9 and 10 of the test cable drive 5 and the additional cable drive 6 are advantageously driven by electric motors, the rotation speed and torque of which can be variably and precisely controlled via a frequency inverter in order to make it possible to set the desired cable load on the test cable 7 by means of the interaction of the two cable drives. The test cable and additional cable drives 5 and 6 in this case are advantageously controlled in an alternating manner by an electronic control device 17 in order to make it possible to variably adjust the load applied to the test cable 7.

In particular, the following load states and/or load cycles can be executed for the test cable 7 by means of the separately controllable test cable and safety cable drives 7 and 8:

Hoisting and lowering of the test load 4 with a full load on the test cable 7. In this case, the additional cable drive 6 is only operated with a very minimal tension on the cable, such that the safety cable 8 substantially only follows.

Hoisting of the test cable 7 with a full load, and lower without a load on the test cable 7. For this purpose, the test load is transferred at the uppermost position from the test cable drive 5 to the additional cable drive 6. The hoisting takes place only by the test cable drive 5, while the lowering takes place only by the additional cable drive 6.

Hoisting of the test cable 7 with no load, and lowering with a full load on the test cable 7. The test load 4 in this case is only hoisted by the additional cable drive 6 alone, which transfers the load when in the uppermost position to the test cable drive 5. During the hoisting, the test cable drive 5 only follows, such that the test cable is spooled out with no load, while during the lowering, the safety cable 8 is spooled in with no tensile force and/or with a very minimal resistance.

The transfer of the test load 4 from the test cable drive 5 to the additional cable drive 6, or in reverse from the additional cable drive 6 to the test cable drive 5 can occur at different hoist heights of the test load 4.

The loading of the test cable drive 5 can also be variably increased or reduced during a hoisting or lowering process, by means of varying the tensile force of the additional cable drive 6 applied—for example in order to simulate the cable load of a cable drive of a crane boom.

The additional cable drive 6 is advantageously only operated with a minimal cable tension by the control device 17 if the test cable drive 5 is operated with a full load, said minimal cable tension being necessary for a good winding of the cable. In contrast, when the additional cable drive 6 is operated with a full load, the test cable drive 5 is advantageously only operated with a minimal load and/or minimal cable tension in order to ensure a cable winding on the winch 9 of the test cable drive 5.

Regardless of which test mode is carried out, the additional cable drive 6 and the safety cable 8 always assume a complete safeguarding function, such that the load cannot be dropped should the test cable 7 break. The winch 10 of the test cable drive 5 in this case can advantageously have an additional secondary brake on the drum. The cable tension and the load speed are advantageously monitored by the control device 17 using suitable sensors or detection means. If the allowed values are exceeded, the test stand is advantageously automatically halted.

As FIG. 2 shows, the test cable 7 can be operated according to another test mode on the cable test stand 1, even with another clamping. In particular, the test cable 7 can be routed from the winch 9 of the test cable drive 5, via the deflection system having the deflector rolls 11 and 12, and the cable reeving 13, which in turn can have a single-pass or multi-pass roller packet 14 and 15, via further deflector rolls 18 and 19, to the winch 10 of the additional cable drive 6. Said winch 10 of the additional cable drive 6 in this case can be the winch shown in FIG. 1, from which the safety cable is spooled out. However, an additional winch and/or an additional cable drive can also be included such that the different test modes can be carried out without modification and/or rewinding of the cable. In order to realize the test cycles named above, which are described in the context of FIG. 1, it is only necessary to halt the one additional drive on which the test cable is spooled, such that the safety cable is operated by means of the additional cable drive, while in contrast, for the test modes according to FIG. 2, the safety cable is merely following. However, for the test modes according to FIG. 2, operation can proceed without the safety cable, because the test load 4 is advantageously only hoisted a slight distance, such that if the cable breaks, a fall cannot have serious consequences.

As FIG. 2 shows, the test cable 7 can be elevated at a slight distance above the ground by the two test cable- and additional cable drives 5 and 6, by means of one or both of the named drives. In this state, the test cable 7 can be spooled back and forth from one of the winches 9 to the other winch 10 and/or the opposite, wherein the full test load 4 is applied to the test cable 7. The spooling of the maximum cable length in this case is advantageously independent of the height of the cable test stand 1, and is substantially only dependent on the cable storage capacity of the drum. As a result, it is particularly possible to test the cable spooling behavior on the drum with multiple wound layers.

In addition, however, different load cycles can be carried out, particularly in that the test load 4 is lower entirely or partially to the ground for individual spooling processes or segments of a spooling process. The test load 4 in this case can advantageously be composed of multiple partial loads, such that different load states can be generated on the test cable 7 according to how many partial loads are set down on the ground. As FIG. 2 shows, the test load 4 in this case can advantageously comprise at least two, and advantageously three or more partial loads 4.1, 4.2, and 4.3, which are advantageously connected to each other in the manner of a chain. The connection of the partial loads to each other in this case is advantageously realized in that, when a partial load is lowered to the ground, the partial load positioned directly above the same is still positioned at a distance from the ground and/or the partial last below. As such, an advantageous clearance is included between the partial loads, which makes it possible to set down multiple partial loads on the ground without determining too exactly a particularly hoist height, while the other partial load or the other partial loads are still held aloft. By way of example, the partial loads can be suspended on each other by means of bending-elastic or flexible tensile means such as ropes or chains or belts, by way of example. As an alternative or in addition thereto, the connection means can also have hinge points which can slide or can change position in another manner, for example in such a manner that pull rods are guided in a limited sliding motion on one of their ends in a hinge device which is like a longitudinal groove.

The following test modes can advantageously be carried out by the control device 17:

A cable spooling process under a full load, from the winch 9 of the test cable drive 5 to the winch 10 of the additional cable drive 6, and vice-versa—likewise under a full load. The test cable in this case always has the complete load as a result of the hoisted test load 4. A corresponding cable spooling process under load is also possible with a partial load, in that the partial load 4.1 and/or the partial load 4.2 is set down on the ground, and only the partial load 4.3 and/or the same together with the partial load 4.2 is still held aloft.

A cable spooling process under a full load, from the winch 9 of the test cable drive 5 to the winch 10 of the additional cable drive 6, and a return spooling from the winch 10 of the additional cable drive 6 to the winch 9 of the test cable drive 5 with no load. For the return spooling with no load, in this case the partial test loads 4.1 and 4.2 are advantageously set down on the ground, and only the uppermost partial test load 4.3 is held aloft, in order to ensure a minimum cable tension for an adequate spooling of the cable.

A cable spooling process with no load, from the winch 9 of the test cable drive 5 to the winch 10 of the additional cable drive 6, and a return spooling in the reverse direction from the winch 10 of the additional cable drive 6 to the winch 9 of the test cable drive 5 under a full load or a partial load. For this spooling process with no load, once again only the uppermost partial load is advantageously held aloft, in order to ensure the necessary cable tension for the spooling thereof.

The load changes resulting from one or more of the partial loads being set down, or one or more additional partial loads being hoisting, can be realized at different cable winding lengths and at different test loads, by different number of partial loads set down, whereby it is possible to create varying load cycles for different test cable segments and/or with different loads.

In order to be able to monitor and/or detect parameters of said test cable which are relevant for the replacement age, a detection device 102 is included which can be arranged on the cable test stand and which can be connected to the electronic cable test stand control device 131, or can be integrated into the same, together with an evaluation device 103.

Figure 3:
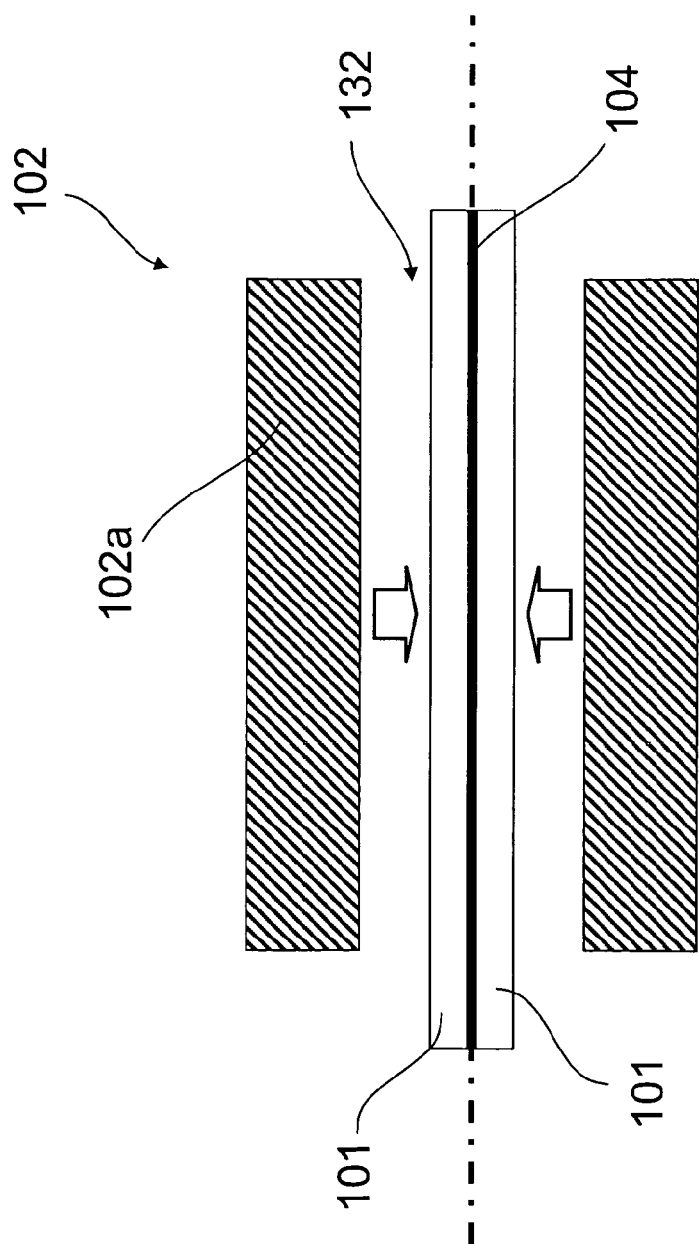
FIG. 3 shows a schematic illustration of detection means of the cable test stand in the previous figures, for the magnetic-induction monitoring of changes of an indicator profile embedded in the test cable.
Figure 4:
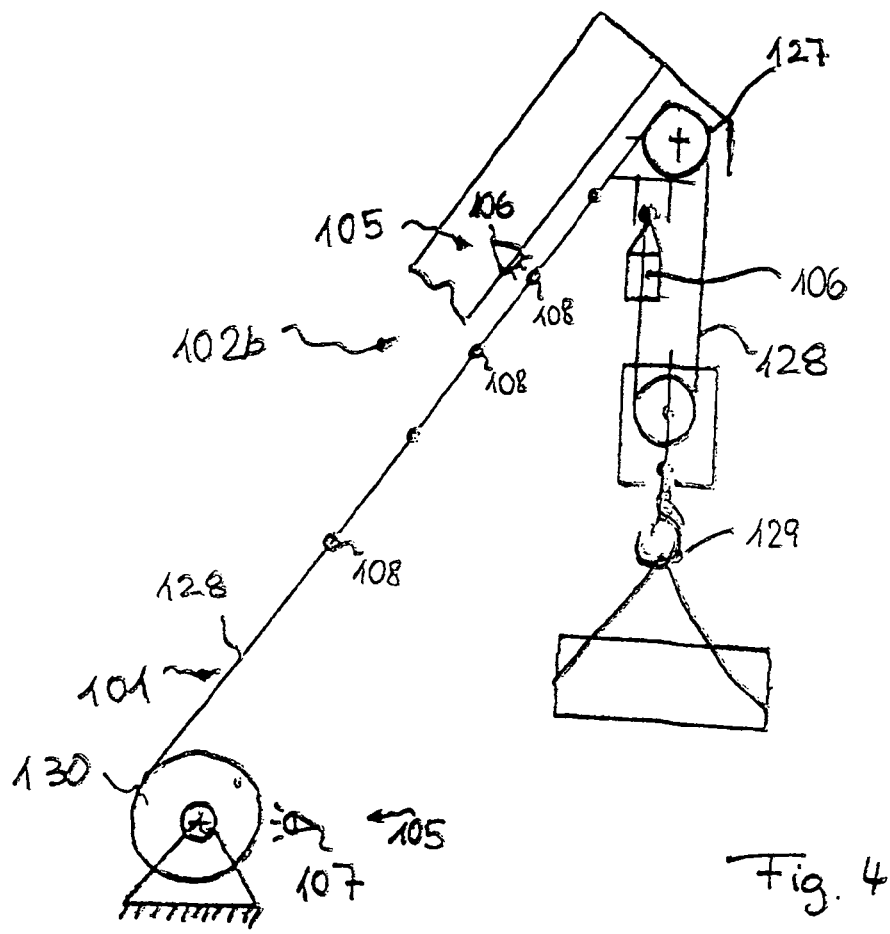
FIG. 4 shows a schematic illustration of detection means of the cable test stand in FIGS. 1 and 2, for the detection of an elongation of the test cable.
Figure 5:
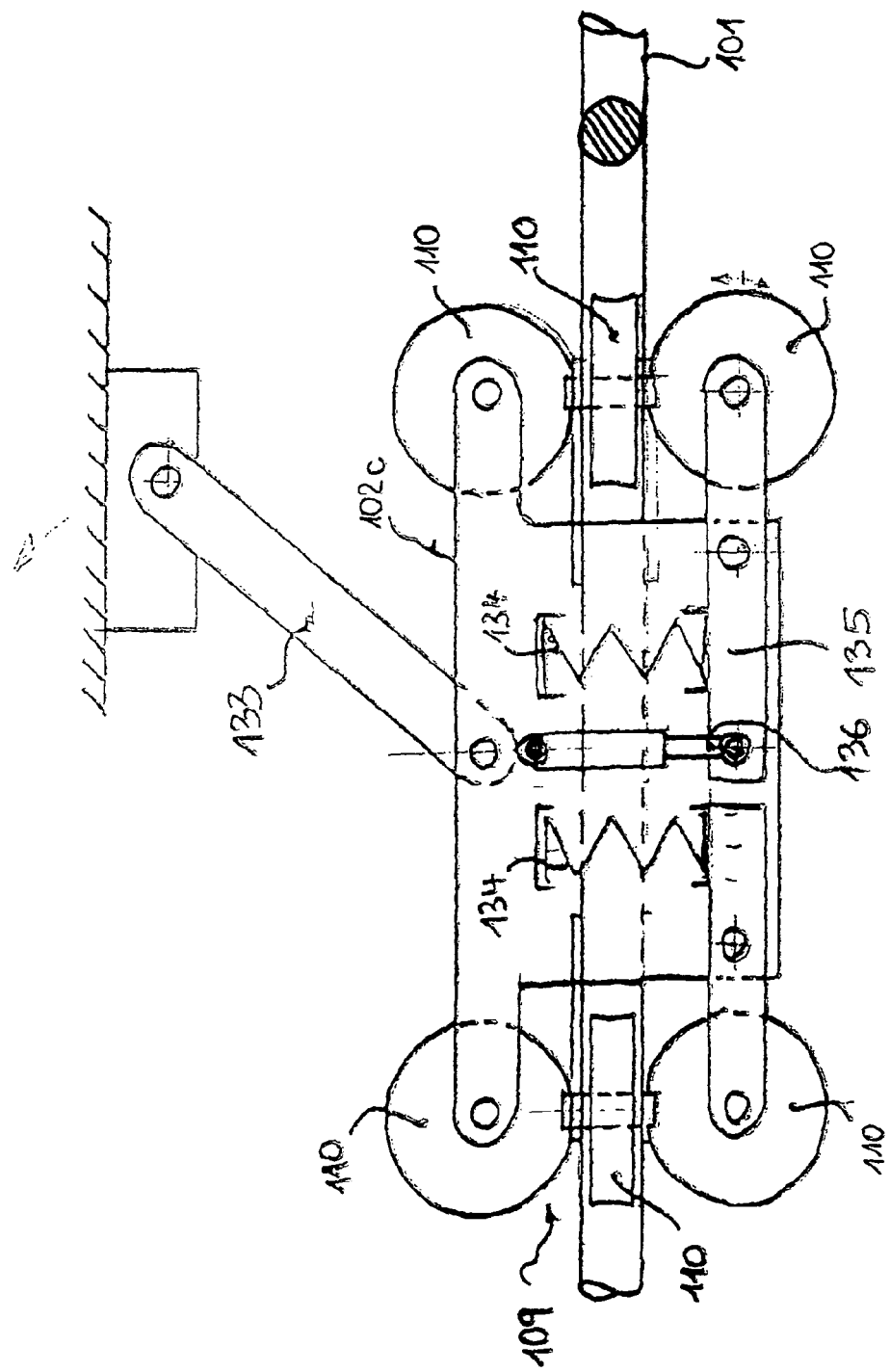
FIG. 5 shows a schematic illustration of detection means for the detection cross-section changes of the test cable on the cable test stand in FIGS. 1 and 2.

As shown in FIGS. 3-5, said detection device 102 in this case advantageously has different detection means in order to detect different parameters of the test cable 101 in different ways. According to FIG. 3, said detection device 102 can have detection means 102a which work magnetically, and which detect changes in an indicator profile 104 which is embedded in the test cable 101, said indicator profile [104] being magnetically conductive and/or being designed to influence a magnetic field and/or to be magnetizable, and being able to be braided into the cable. By way of example, said indicator profile 104 can be arranged in the core in the braiding or between strands, wherein the indicator profile 104 itself can have any cross-section shape, and can be advantageously configured with a round cross-section. In particular, said indicator profile 104 can be formed from a continuous metallic material such as a wire, wherein the indicator profile 104 is advantageously made such that it is designed to be less resistant to cable loads, expansions, tensile forces, bending, twisting, temperature and of relevant properties than the fibers of the test cable 101 and/or the test cable 101 itself, such that the indicator profile 104 fails before the test cable 101 fails.

Said magnetic detection means 102a, which can comprise a magnetic field sensor by way of example, detect the changes in a magnetic field which is applied to said indicator profile 104 or is generated by the same. A break in said indicator profile 104 particularly leads in this case to changes in said magnetic field 132, such that a detection of the corresponding characteristic magnetic field alteration can be used to conclude that a break has occurred in the indicator profile 104, and therefore in turn that the test cable 101 is due for replacement.

In order to be able to determine in which region of the test cable 101 the break of the indicator profile 104 occurs, a cable path meter can be functionally assigned to the detection device 102 and/or the magnetic detection means 102a thereof, said cable path meter being implemented by suitable cable path detection means 105—for example in that a rotational position sensor 107 (cf. FIG. 4) which is functionally assigned to the cable winch outputs the rotary position of the cable winch, or position sensors 106 (cf. FIG. 4) detect characterizing cable segments at a certain position and/or positions at which said magnetic detection means 102a report the failure. From the known position of the detection means 102a, the evaluation device 103 can exactly determine where the failure has been detected. Because of the remaining service life of the high-strength test cable, the necessary period for the exchange of the test cable 101 is advantageously displayed on, for example a monitor of the cable test stand controller. If an exchange is not made in the pre-specified time, the cable test stand control device 131 can automatically halt the cable test stand for safety reasons.

As FIG. 4 shows, the detection device 102 named above also advantageous has detection means 102b for the purpose of determining an elongation of the test cable 101 occurring more and more during operation. In this case, a particular position can be assumed by the test cable 101—for example by moving directly to the upper switch-off point at which the load hook 129 has reached the highest possible position, which can be detected by an end switch or another position sensor 106, by way of example. If said position sensor 106 reports to the detection means 102b that the predetermined cable position has been reached, the position of the cable winch is detected and/or determined by a cable winch position sensor 107. This measurement is initially carried out upon the first start-up of the cable test stand. Upon later measurement, if another cable winch position arises when the predetermined cable position is reached, the deviation of the cable drum position when the same cable point is reach is a measure for the elongation of the test cable 101 which has occurred.

In this method for detecting the cable elongation by measuring the increasing rotation of the drum to the switch-off point, it must be noted that this is an average value of the cable elongation. The cable expansion is dependent on the load and the duration of the load. When a load is moved—for example by "hoisting"—then the cable region which is not wound on the cable drum always has the full and longest load, until the load is set down again. In the cable region which is spooled on the drum, the cable tension continuously drops, as does the expansion force as a result. As such, the expansion of the cable outside of the cable drum runs approximately constantly, and the cable [in this region] always receives the maximum load. The existing tensile load drops continuously for the cable which is wound on the drum, because the cable load under tension drop to approximately zero after several windings. The boundary of allowable elongation can be determined in this method by an expansion distribution factor with respect to the total length of the cable, in order to obtain adequate reliability for the time point of the replacement age of the test cable 101.

A further method for testing the cable elongation with respect to replacement age is based on signaling devices 108 and/or indicator which actively or inactively output signals. These indicators are integrated into the cable at approximately the same intervals. By way of example, an electrical-electronic measuring device, for example in the form of a position sensor 106, detects the point of the indicator, and measures the longitudinal distance to the next indicator at a constant cable speed. As such, the length of the cable can be divided into any number of measurement point, and with this method an evaluation is obtained on the expansion profile of the cable over the entire cable length, and a measuring device detects the cable region in which the threshold has been reached.

As FIG. 5 shows, the detection device 104 can also advantageously have detection means 102c for the purpose of determining changes in the cable cross-section of the test cable 101. Said detection means 102c advantageously detect the cable diameter in at least two planes which can be advantageously perpendicular to each other in order to be able to determine the cable cross-section surface area from the multiple cable diameters even when there are changes in the cable cross-section shape which do not yet pose a risk. This is based on the background that high-strength test cables 101 tend to become oval in cross-section when subjected to transverse loads such as occur on the deflector rolls 127 or on the cable winches 125 and/or 130, and this oval shape in and of itself does not result in a negative impact on the strength of the cable. What is critical is when the cable cross-section surface area decreases.

In the embodiment in FIG. 5, for this purpose the cable diameters are mechanically scanned in planes which are perpendicular to each other by means of pairs of clamping means in the form of cable rolls 110 which are pressed against the surface of the test cable 101 from opposite sides, such that the clearance between the clamping means in the form of the cable rolls 110 is a measure for the corresponding cable diameter.

As FIG. 5 shows, the detection means 102c overall are mounted in a manner allowing movement perpendicular to the longitudinal direction of the cable, such that perpendicular movements of the test cable 101 do not have an effect on the measurement results. In the embodiment shown, the entire device in this case is suspended via a pivoting plane and/or a lever linkage 133 in a manner allowing perpendicular movement (cf. FIG. 5).

The measuring device advantageously has, in one plane, at least two rolls in the front region and two rolls in the rear region, of which in each case the lower roll gently clamps the cable 101 by means of springs 134, and therefore detects the cable diameter. One of these lower, spring-loaded rolls 110 has a rotary axis and a lever 135, via which the measured cable diameter is transmitted to a path sensor 136 and therefore is evaluated. The measuring device also has guide rolls laterally to the cable, such that the measuring device is guided over the cable, and potential cable vibrations have no influence on the measured value. The measuring device is suspended via a lever in a hinged manner to the steel construction of the cable test stand, in order to compensate for movements. The cable measured is advantageously carried out via at least two planes of the cable which are offset by 90°, such that the cable diameter is tested over four areas. A further offset arranged—for example for six areas—is possible. The measurement over 2-4-6, etc. areas can be constructively included in a measuring device, or by the arrangement of multiple measuring devices.

A further possibility consists in the use of optical test devices which detect and evaluate a cable diameter change with respect to the circumference. If the allowed diameter deviation is exceeded, a warning signal is output and the position is saved via the drum rotation speed sensor 107.

In addition, said detection device 102 have also advantageously have detection means 102d for the purpose of detecting the load spectrum acting on the respective test cable 101, wherein in this case it is possible to advantageously detect at least the tensile load applied to the cable, and the number of flex cycles, and also to advantageously detect other parameters which influence the fatigue limit, such are multi-layer spooling, environmental influences, temperature, transverse loading, and others.

For the purpose of determining these parameters, said detection means 102d have corresponding sensors, the signals of which [are processed] in said evaluation device 103. In particular, a load sensor can detect the continuous load over the operating time of the cable. In addition, a rotational distance sensor on the respective winch drum can advantageously measure the length of the cable which is loaded. In all, it is possible to determine a load spectrum, for example in the form of a stress cycle curve, which can be specified as a maximum load spectrum for the test cable 101.

Numerous characteristics and advantages have been set forth in the foregoing description, together with details of structure and function. While the invention has been disclosed in several forms, it will be apparent to those skilled in the art that many modifications, additions, and deletions, especially in matters of shape, size, and arrangement of parts, can be made therein without departing from the spirit and scope of the invention and its equivalents as set forth in the following claims. Therefore, other modifications or embodiments as may be suggested by the teachings herein are particularly reserved as they fall within the breadth and scope of the claims here appended.

The invention claimed is:

1. A cable test stand for testing a test cable to establish service life, replacement age, allowed number of flex cycles, and/or winding behavior comprising:
    a deflection system comprising:
        at least one deflector roll to deflect the test cable,
        a test cable drive to wind and unwind the test cable via the deflection system, and
        one test load to load the test cable,
    an additional cable drive for the purpose of winding and unwinding a safety cable and/or the test cable, and
    a control device for the purpose of controlling the additional cable drive and/or the test cable drive in a manner wherein the two are adjusted to each other,
    wherein the load of the test cable can be adjusted differently for one or more of different test cable segments, different winding directions, different winding cycles, and different phases of a winding cycle.

2. The cable test stand according to claim 1, wherein the control device is designed in such a manner that the load of the test cable can be varied by stronger and/or weaker application of the additional cable drive during a winding process.

3. The cable test stand according to claim 1, wherein the control device is designed in such a manner that the load of the test cable can be varied by stronger and/or weaker application of the additional cable drive to different segments of the test cable and/or different positions in the vertical path traveled by the test load.

4. The cable test stand according to claim 1, wherein the control device is designed in such a manner that it is possible to go through testing cycles with hoisting under full load and lowering without a load, or with a reduced load, and/or to go through testing cycles with hoisting with no load or with a reduced load, and lowering with full load.

5. The cable test stand according to claim 1, wherein the test cable and the safety cable each have their own cable reeving in the test load, and/or the test cable can be wound and unwound by the test cable drive, and the safety cable can be wound and unwound by the additional cable drive, in such a manner that it is possible to hoist and/or lower the test load, as desired, by the test cable alone, or by the safety cable alone, or by both the test cable and the safety cable.

6. The cable test stand according to claim 1, wherein the test cable is routed via a cable reeving to the test load, and via the deflection system to both the test cable drive and to the additional cable drive or to a further additional cable drive,
    wherein the test cable drive and the additional cable drive can be operated in opposite directions with respect to each other in such a manner that the test cable can be wound by the test cable drive to the additional cable drive and/or vice-versa,
    wherein the test load preferably has multiple partial test loads which are connected to each other in such a manner that the partial test loads can be set down on the ground individually or in groups, and
wherein at least one other partial test load is held aloft.

7. The cable test stand according to claim 1, wherein the test cable drive and/or the additional cable drive comprises an electric motor, the rotation speed and/or torque of which can be variably controlled by means of a frequency rectifier.

8. The cable test stand according to claim 1 further comprising:
a detection device for the purpose of detecting at least one cable parameter, and
an evaluation device for the purpose of evaluating the cable parameter and for the purpose of providing a removal signal which characterizes the replacement age and/or the maximum service life according to the evaluation of the cable parameter,
wherein the detection device has multiple detection means with different designs for the purpose of detecting multiple, different cable parameters magnetically, mechanically, optically, and/or electronically, and
wherein said cable parameters can be evaluated by the evaluation device individually and/or in combination with each other for the purpose of determining the replacement age and/or the maximum service life and/or the allowable number of flex cycles.

9. The cable test stand according to claim 8, wherein the evaluation device emits a removal signal when at least one of the detected cable parameters or the alteration thereof exceeds an associated threshold, and also when an indirect summed parameter or the alteration thereof, said parameter being indirectly derived from all or from one of the detected cable parameters, exceeds an associated threshold.

10. The cable test stand according to claim 8, wherein the detection device has detection means for the purpose of detecting an alteration of an indicator profile which is embedded in the fiber rope and comprises a material which is different from the rope fibers,
wherein the detection means are designed to work magnetically, and comprise a magnetic field sensor, and
wherein the indicator profile comprises a material which influences a magnetic field and/or is magnetically conductive and/or can be magnetized.

11. The cable test stand according to claim 8, wherein the detection device has detection means for the purpose of detecting an elongation of the fiber rope.

12. The cable test stand according to claim 11, wherein the detection means have a position sensor for the purpose of detecting a predetermined cable point at a predetermined position of an upper switch-off point for the load hook of the test load, as well as a cable winding position sensor for the purpose of detecting the winding position when the predetermined cable point position is reached, and the evaluation device monitors the change in the winding position, and/or the detection means have multiple signaling devices for the purpose of detecting the elongation in the fiber rope, said signaling devices being distributed over the length thereof, and have determination means for the purpose of determining the distance between each pair of signaling devices, and the evaluation device evaluates the change in the determined distance between each pair of signaling devices.

13. The cable test stand according to claim 8, wherein the detection device has cross-section determination means for the purpose of determining the cable cross-section, and the evaluation device evaluates the determined cable cross-section and monitors for changes,
wherein the cross-section determination means particularly has diameter detection means for the purpose of detecting the cable diameter in at least two different planes, and determines the cable cross-section surface area from the at least two determined cable diameters, and
wherein the diameter detection means has at least one pair of clamping means which can be elastically pre-tensioned against the cable parameter and which are suspended in a manner allowing movement perpendicular to the longitudinal direction of the cable, as well as distance measuring means for the purpose of measuring the distance of the pairs of clamping means from each other.

14. The cable test stand according to claim 8, wherein the detection device has a load spectrum counter for the purpose of detecting the load spectrum acting on the fiber rope, including the tensile load on the cable and the number of flex cycles.

15. The cable test stand according to claim 8, wherein cable path- and/or cable position detection means for the purpose of determining the cable segment in which changes occur in the detected cable parameter, are functionally assigned to the detection device, and the evaluation device provides a cable segment signal, together with the removal signal, which indicates which cable segment is due for replacement.

16. A cable test stand for testing a test cable comprising:
a deflection system comprising:
at least one deflector roll to deflect the test cable,
a test cable drive to wind and unwind the test cable, and
one test load to load the test cable,
an additional cable drive to wind and unwind one or both of a safety cable and the test cable, and
a control device to control one or both of the additional cable drive and the test cable drive in a manner wherein the two are adjusted to each other,
wherein the load of the test cable can be adjusted differently for one or more of different test cable segments, different winding directions, different winding cycles, and different phases of a winding cycle.

17. The cable test stand according to claim 16, wherein the control device is designed in such a manner that the load of the test cable can be varied by stronger and/or weaker application of the additional cable drive during a winding process,
wherein the control device is designed in such a manner that the load of the test cable can be varied by stronger and/or weaker application of the additional cable drive to different segments of the test cable and/or different positions in the vertical path traveled by the test load, and
wherein the control device is designed in such a manner that it is possible to go through testing cycles with hoisting under full load and lowering without a load, or with a reduced load, and/or to go through testing cycles with hoisting with no load or with a reduced load, and lowering with full load.

18. The cable test stand according to claim 16 further comprising:
a detection device to detect at least one cable parameter, and
an evaluation device to evaluate at least one of the at least one cable parameters and provide a removal signal that characterizes the replacement age and/or the maximum service life according to the evaluation of the at least one of the at least one cable parameters.

19. The cable test stand according to claim 18, wherein the detection device has multiple detection means to detect multiple, different cable parameters magnetically, mechanically, optically, and/or electronically, and wherein the cable parameters can be evaluated by the evaluation device individually and/or in combination with each other for the purpose of determining the replacement age and/or the maximum service life and/or the allowable number of flex cycles.

* * * * *